(12) United States Patent
Wojton et al.

(10) Patent No.: US 8,693,788 B2
(45) Date of Patent: Apr. 8, 2014

(54) ASSESSING FEATURES FOR CLASSIFICATION

(75) Inventors: Maciej Wojton, Roslyn Heights, NY (US); Nikolai Kabelev, Irvington, NY (US)

(73) Assignee: MELA Sciences, Inc., Irvington, NY (US)

( * ) Notice: Subject to any disclaimer, the term of this patent is extended or adjusted under 35 U.S.C. 154(b) by 294 days.

(21) Appl. No.: 12/852,195

(22) Filed: Aug. 6, 2010

(65) Prior Publication Data

US 2012/0033863 A1 Feb. 9, 2012

(51) Int. Cl.
*G06K 9/62* (2006.01)
*G06K 9/00* (2006.01)
*G06K 9/68* (2006.01)

(52) U.S. Cl.
USPC ............ 382/209; 382/133; 382/224; 382/226

(58) Field of Classification Search
USPC .......... 382/126–133, 224, 226–230, 205, 209
See application file for complete search history.

(56) References Cited

U.S. PATENT DOCUMENTS

| | | | |
|---|---|---|---|
| 5,522,011 A | 5/1996 | Epstein et al. | |
| 5,572,689 A * | 11/1996 | Gallup et al. | 712/200 |
| 6,081,612 A | 6/2000 | Gutkowicz-Krusin et al. | |
| 6,208,749 B1 | 3/2001 | Gutkowicz-Krusin et al. | |
| 6,307,957 B1 | 10/2001 | Gutkowicz-Krusin et al. | |
| 6,850,252 B1 * | 2/2005 | Hoffberg | 715/716 |
| 7,570,816 B2 * | 8/2009 | Bargeron et al. | 382/224 |
| 2002/0010691 A1 * | 1/2002 | Chen | 706/20 |
| 2004/0059697 A1 | 3/2004 | Forman | |
| 2008/0147788 A1 * | 6/2008 | Omoigui | 709/203 |
| 2008/0170770 A1 * | 7/2008 | Suri et al. | 382/128 |
| 2008/0214907 A1 | 9/2008 | Gutkowicz-Krusin et al. | |
| 2008/0240581 A1 * | 10/2008 | Napoletani et al. | 382/224 |
| 2008/0292194 A1 * | 11/2008 | Schmidt et al. | 382/217 |
| 2008/0306898 A1 | 12/2008 | Tsypin et al. | |
| 2008/0319747 A1 | 12/2008 | Kompe et al. | |
| 2009/0022665 A1 * | 1/2009 | Isabelle et al. | 424/9.1 |
| 2009/0024555 A1 * | 1/2009 | Rieck et al. | 706/54 |
| 2009/0154781 A1 | 6/2009 | Bogdan | |
| 2009/0257662 A1 * | 10/2009 | Rudin et al. | 382/218 |
| 2009/0276384 A1 | 11/2009 | Harris | |
| 2010/0098306 A1 * | 4/2010 | Madabhushi et al. | 382/128 |

FOREIGN PATENT DOCUMENTS

WO WO 2009/079367 6/2009

OTHER PUBLICATIONS

Dash et al,. "Feature Selection for Classification," *Intelligent Data Analysis*, 1:131-156 (1997).

(Continued)

*Primary Examiner* — Matthew Bella
*Assistant Examiner* — Weiwen Yang
(74) *Attorney, Agent, or Firm* — Fish & Richardson P.C.

(57) ABSTRACT

Among other things, a degree is determined to which values of a feature that characterizes cases correctly predict classes to which cases belong, the degree depending on a combination of at least two factors that include: (a) uncertainty about the values that the feature will have depending on knowledge about classes to which cases belong, and (b) comparison of one or more first values of the feature that are associated with cases that belong to a first class with one or more second values of the feature associated with cases belonging to a second class.

23 Claims, 12 Drawing Sheets

(56) References Cited

OTHER PUBLICATIONS

Dhir et al., "Efficient feature selection based on information gain criterion for face recognition," *Proceedings of the 2007 International Conference on Information Acquisition*, 523-527 (2007).

Duda et al., "Mathematical Foundations," 2nd ed. Wiley-Interscience, 187-188 (2001).

Duda et al., "Metrics and Nearest-Neighbor Classification," 2nd ed. Wiley-Interscience, 632 (2001).

Guyon et al., "An Introduction to Variable and Feature Selection," *Journal of Machine Learning Research*, 3:1157-1182 (2003).

He et al., "Optimising the Distance Metric in the Nearest Neighbour Algorithm on a Real-World Patient Classification Problem," N. Zhong and L. Zhou (Eds.), 365-369 (1999).

Jing et al., "Ontology-based Distance Measure for Text Clustering," *2006 Society for Industrial and Applied Mathematics Conference*[online], [retrieved on Jul. 13, 2010]. Retrieved from the Internet: http://www.siam.org/meetings/sdm06/workproceed/Text%20Mining/jing1.pdf, 8 pages.

Shannon et al., "The mathematical theory of communication," *University of Illinois Press*, Urbana, Illinois (1949), republished in 1990 by Dover Publications, Inc, and in 1998 by the University of Illinois.

Shannon et al., "The mathematical theory of communication," Reprinted with corrections from *The Bell System Technical Journal*, 27:379-423, 623-656 (Jul., Oct. 1948) [online], [retrieved on Sep. 8, 2010]. Retrieved from the Internet: http://cm.bell-labs.com/cm/ms/what/shannonday/paper.html, 55 pages.

International Search Report and Written Opinion for App. Ser. No. PCT/US2011/046640, mailed Feb. 28, 2012.

Australian Office Action from App. Ser. No. 2011285628, dated Apr. 7, 2013, 4 pages.

International Preliminary Report on Patentability for App. Ser. No. PCT/US2011/046640, dated Feb. 13, 2013.

* cited by examiner

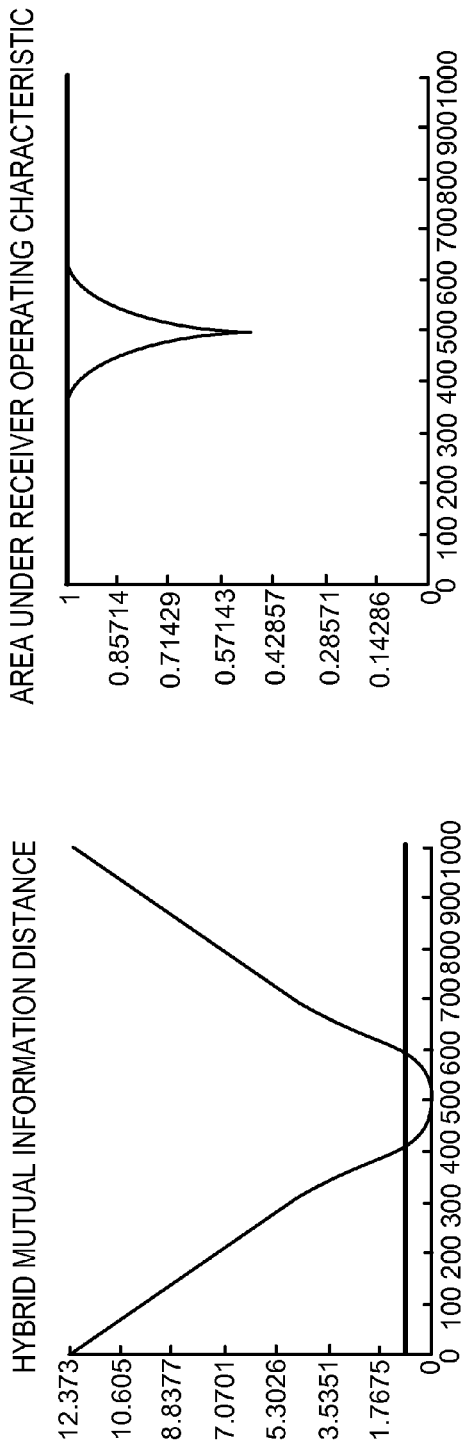
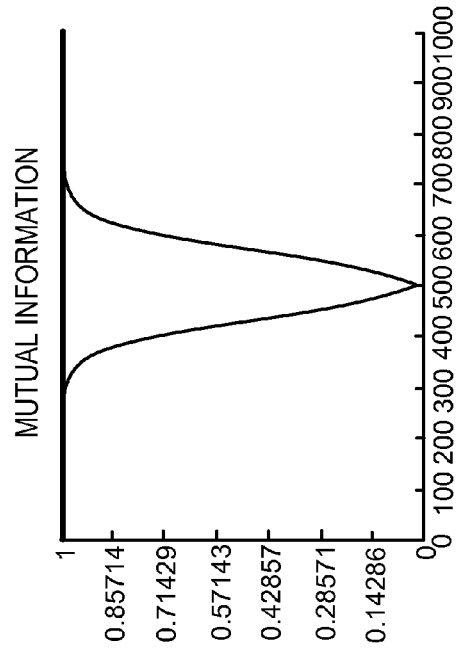
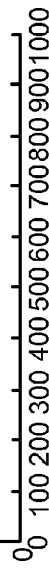
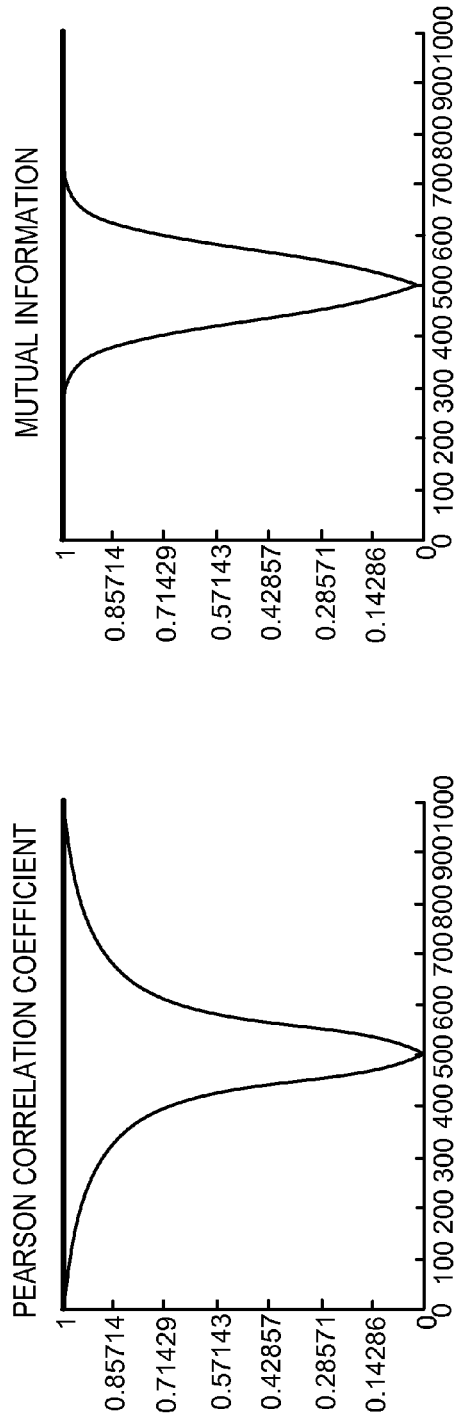
FIG. 9A  
FIG. 9B  
FIG. 9C  
FIG. 9D

ASSESSING FEATURES FOR CLASSIFICATION

BACKGROUND

This description relates to assessing features for classification.

Classifications may be useful, for example, in the medical field, to classify an image, a test result, a genetic sequence, or a radiograph as being indicative of either a disease or no disease. In the security field, it may be useful to classify an x-ray as one that indicates either that a threatening object was present in the space imaged or that no threatening object was present. In the communications field, it may be useful to classify a sound as being a human voice or as being other noise.

Frequently, classification uses values of features, each feature relating to a characteristic of data that represents a case being examined (e.g., a lesion, a potential bomb, or a sound signal). For example, features of a multispectral image (e.g., of a skin lesion or of suitcase contents) may include an area, a contrast, a perimeter length, a color variability, a color intensity, a perimeter-to-area ratio, an asymmetry, a border irregularity, and a diameter of the lesion. Features of a sound file may include an amplitude at a frequency or a variation in volume or frequency amplitude across time. A value for each of the features may be determined for each case (e.g., for each lesion based on an image of the lesion) that belongs to a set of cases. For example, if there are ten images (cases) of skin lesions in a data set, a value for the area may be determined for the lesion of each image.

Different features may be more or less useful in effectively classifying cases of a data set (e.g., whether a lesion is melanoma, whether a suitcase-content item is a bomb, or whether a sound signal is a human voice).

SUMMARY

In general, in an aspect, a degree is determined to which values, of a feature that characterizes cases, correctly predicts classes to which cases belong, the degree depending on a combination of at least two factors that include: (a) uncertainty about the values that the feature will have depending on knowledge about classes to which cases belong, and (b) comparison of one or more first values of the feature that are associated with cases that belong to a first class with one or more second values of the feature associated with cases belonging to a second class.

Implementations may include one or more of the following inventive features. The uncertainty is represented by a mutual information measure. The comparison includes a distance measure. The distance measure is normalized. The uncertainty includes an entropy of values of the feature. The uncertainty includes an uncertainty about the values of the feature when the classes to which the cases belong are known, and an uncertainty about the values of the feature when the classes to which the cases belong are not known. The degree is determined as a score. The comparison of one or more first values of the feature with one or more second values of the feature includes determining differences between first values and second values. The comparison of one or more first values of the feature with one or more second values of the feature includes a comparison of a first value of the feature with two or more second values of the feature. The degree is determined with respect to values of more than one such feature, the degree depending on: (a) uncertainty about values that the more than one such feature will have depending on the classes to which cases belong, and (b) comparison of one or more first values of the more than one such feature that are associated with cases that belong to a first class with one or more second values of the more than one such feature associated with cases belonging to a second class. The comparison includes a metric distance between the one or more first values of the feature and the one or more second values of the feature. The cases include cases in a communications field (e.g., sound files), a medical field (e.g., image files), a computer-vision field (e.g., image files of undersea growth), a computer-security field (e.g., strings of text), a voice-recognition field (e.g., sound files), or a genetic field (e.g., strings of text representing genetic sequences). The cases include medical cases. The cases include skin lesions and the classes include melanoma and non-melanoma. A first degree is determined to which a value of a first feature that characterizes cases correctly predicts classes to which a particular cases belongs; a second degree is determined to which a value of a second feature that characterizes cases correctly predicts classes to which a particular cases belongs; and the determined degrees are compared. A feature is selected for use in classification, based at least in part on the determination of the degree. The cases are represented by digital images and the features relate to what is portrayed in the digital images. The values include measures of features that appear in the digital images. The uncertainty is represented by an accuracy measure.

In general, in an aspect, a degree is determined to which values, of a feature that characterizes cases, correctly predict classes to which cases belong. The degree is determined based on a combination of at least two factors selected so that the degree: substantially corresponds to a fixed number when distributions of values for cases in the two classes completely overlap, and depends, in a non-saturating manner, on a separation between the distributions.

These and other aspects, features, and implementations, and combinations of them, can be expressed as methods, means or steps for performing functions, business methods, program products, compositions, apparatus, systems, components, and manufactures, and in other ways.

Other aspects, inventive features, advantages, and implementations will be apparent from the description and from the claims.

DESCRIPTION

FIGS. 1, 4, and 6 are flow diagrams.
FIGS. 2, 3, and 5 are explanatory diagrams.
FIG. 7 is a perspective view of hardware.
FIGS. 8A through 8J are graphs.
FIGS. 9A through 9H are graphs of separation scores.
FIG. 10 is a block diagram.

As shown in FIG. 10, a training data set 10 includes cases 12 (e.g., skin lesions represented in images 14) with corresponding classifications 16, known to be correct, for each of the cases, into one or another of different classes 18 (e.g., melanoma or non-melanoma). In the training data set, each case is characterized by values 20 that are derived from the data representing the case and are values for corresponding features 22 (e.g., asymmetry, border irregularity, color variability, diameter of the lesion, and others identified in U.S. Pat. Nos. 6,081,612, 6,208,749, and 6,307,957; United States Patent Publications US 2008/214,907 and US 2009/154,781; and World Intellectual Property Organization Publication WO 2009/079,367 that might be under consideration as potentially useful for accurate classification of the cases among the classes 18. These features (and combinations of them) can be analyzed to produce scores 24 that represent an expected relative usefulness of the features in classifying cases. The scores can serve as a basis for selecting a preferred feature 26 (or preferred set of features) for use in classifying cases that are in a test data set 28 (labeled as a non-training data set in FIG. 10), having cases that may be partly or completely distinct from the cases of the training data set 10.

Although we have used the example of classifying lesions between melanoma and non-melanoma based on data derived from images of the lesions, the cases in the training data set may comprise or represent, for example, a wide variety of kinds of data that can be characterized by features, including, for example, images, objects in images, data, numbers, audio signals, radiographs, genetic sequences, gene-expression profiles, electrical signals, or magnetic signals, to name just a few.

The training data set can be considered as including a first subset of cases that could be interpreted, based on values of one or more features, as likely belonging to a particular one of the classes (say non-melanoma), and a second subset of cases that could be interpreted as likely belonging to a second class (say melanoma). Depending on the implementation, cases in the second data subset may be associated with a medical diagnosis (e.g., melanoma), a signal type (e.g., a speech signal), an object (e.g., a human present in image data), or other kinds of information, for example.

As shown in FIG. 1, for purposes of scoring features, selecting one or more preferred features, and constructing a classifier based on the preferred feature or features, a process 100 can be followed that begins with receiving 105 the first subset of cases in the training data set, and receiving the second subset of cases in the training data set 110. Then, the following processes can be applied for each of one or more possibly useful features.

For each feature, a value of that feature is determined 115 for each case that belongs to the first subset of the training data set, thus defining a first subset of feature values (that is, a feature vector). The process is then repeated 120 for that feature for each case that belongs to the second subset of the training data set, thereby defining a second subset of feature values (a second feature vector). Next, a score is determined 125 for the feature based on the first and second subsets of feature values. Feature-value determinations 115 and 120 and score determination 125 are repeated until a score has been determined for each feature or combination of features to be analyzed 130.

The relative scores for the one or more features can then be used to identify 135 a preferred feature or set of features to be used for classification of other cases. The preferred feature or set of features and the related scores are then output 140, and a classifier is constructed 145.

In some instances, the cases in the training data set can be classified perfectly in the sense that all of the cases of the training data set that are interpreted as likely belonging to the second class do, in fact, belong to the second class and none of the cases that are interpreted as likely belonging to the second class belong, in fact, to the first class, and vice versa. In other words, both subsets (and the classes to which they are interpreted as belonging) are void of any falsely classified cases. Perfect classification can be forced to occur by, for example, causally manipulating how the training data set is produced. For example, if classification depended on whether a human is present in an image, the images for which cases are included in the training data can be manipulated by photographing visual scenes that are known to include or known not to include a human. In the case of lesions, the cases for the training data set can be controlled to include only cases for which the actual correct diagnosis (melanoma or non-melanoma) is known.

Conversely, in some instances, the cases in the training data set are imperfectly classified or the accuracy of the classification is unknown, for example, when the training data are not the result of causal manipulation of a situation. For example, humans or other techniques may be used to determine whether a particular skin lesion captured in a photograph represents melanoma. The patient may be tracked or biopsied to further confirm the determination, but even so, false positives or false negatives may occur (e.g., resulting from errors in a biopsy or melanomas that develop subsequently).

In some instances, the two training data subsets include the same number of cases. For example, data in cases of the first data subset may parallel or be matched to data in cases from the second data subset. For example, each case in the first data subset may be associated with a patient, and a corresponding case in the second data subset may be associated with the same patient but obtained under different circumstances. Data in cases of the second subset may have been collected after a diagnosis or from a location of interest (e.g., because of an unusual appearance at the location), while data in cases of the first subset may have been collected prior to a diagnosis or from a different location (e.g., a location with a normal appearance). As another example, data in cases from the first data subset may be "noise" cases associated with a set of experimental conditions, and data in cases from the second data subset may be "noise+signal" cases associated with the same set of conditions.

In some instances, the number of cases in the first training data subset is different from the number of cases in the second training data subset. Different numbers of cases may occur, for example, when data for the two subsets are collected from different populations of settings, individuals, or subjects. Different numbers of cases may also occur, for example, when cases in the two data subsets are generally associated with a single population but the case numbers are nonetheless unequal (e.g., because patients dropped out of a study or because more or less "noise+signal" cases were collected for a given set of conditions than were "noise" cases).

As shown in the example of FIG. 2, cases for a training data set may be obtained by acquiring images 220, and 225, of skin lesions 215$i$ and 215$j$ on two patients 205$_i$ and 210$_j$ (using a digital camera or a multi-spectral image capture device, for example). Analysis (e.g., based on a physician's opinion or on a biopsy) may indicate that the lesion of patient 205$_i$ is not melanoma while the lesion of patient 210$_j$ is melanoma. Thus, the image 220$_i$ may be assigned to a first non-melanoma training data subset, and image 225$_j$ may be assigned to a second melanoma training data subset. While FIG. 2 shows patient 205$_i$ as having a non-melanoma skin lesion, in other instances, the patient may not have any lesion. For example, images of the second data subset may include images of melanoma lesions, while images of the first data subset may include non-lesion images of comparable body parts or from the same patient.

In some implementations, the determinations 115 and 120 (FIG. 1) comprise what may be called operationalizing cases of the training data set. By operationalizing, we mean to include defining a non-measurable, abstract, fuzzy, qualitative, or subjective measure in terms of a measurable, quantitative, more measurable, or more quantitative variables. For example, "asymmetry" may be operationalized to an asymmetry variable defined as $(N_L-N_R)/(N_L+N_R)$ where $N_L$ is a number of pixels associated with a lesion to the left of a long axis and $N_R$ is a number of pixels associated with the lesion to the right of the axis.

In some implementations, these determinations involve reducing the dimensionality of or parameterizing (recharacterizing a case as a template that can be described or mathematically defined by parameters) or are based on a signal-processing analysis. In some implementations, these determinations associate each case of the training data set with one number (i.e., a value for a feature). In some implementations, these determinations associate each case of training data set with more than one number (i.e., a value for each of a combination of features). In some implementations, these determinations comprise pre-processing (e.g., normalizing or imputing missing data) prior to determining values of the feature. In some implementations, the values of the feature are numeric or binary. In some implementations, the values of the feature are of a discrete, finite class (e.g., a class corresponding to low texture, medium texture, or high texture in an image).

In some implementations, the values of the feature are determined for each case of a combined training data set, the combined data set including both the first and second subsets of cases. The values may then be separated (e.g., based on a classification associated with each case of the combined training data set) to define the first and second subsets of feature values.

In some implementations, rather than determining a single value of a feature associated with each case, multiple values may be determined. The multiple values may all relate to a single feature (e.g., values that, taken together describe a lesion asymmetry) or may relate to more than one of the features (e.g., to a lesion asymmetry and to a lesion's color variability).

In FIG. 2, values $x_{1,i}$ and $x_{2,j}$ of a feature are determined based on the data for the respective images $220_i$ and $225_j$. The feature values may be associated with a property of the lesion. For example, the values $x_{1,i}$ and $x_{2,j}$ may comprise or relate to an asymmetry, border irregularity, color variability, or diameter of the lesion. In some instances, values (e.g., $x_{1,i}$) associated with cases from one class (e.g., a non-melanoma class) and values (e.g., $x_{2,j}$) associated with cases from another class (e.g., a melanoma class) may both be values associated with the same feature. For example, both $x_{1,i}$ and $x_{2,j}$ may be numbers representing an asymmetry feature of the lesion. In some instances, images $220_i$ and $225_j$ are digital images. In some instances, images $220_i$ and $225_j$ may be converted into digital images (e.g., by scanning the images into a computer) so that the values $x_{1,i}$ and $x_{2,j}$ may be determined from the digital data derived from images. The images $220_i$ and $225_j$ may be pre-processed (e.g., to adjust for shading, lighting, or scaling effects) before the values $x_{1,i}$ and $x_{2,j}$ are determined.

As shown in FIG. 3, a value of a feature may be obtained for each of the cases that fall into each class. For example, each image 220 from a non-melanoma training subset 222 may be associated with a value of a feature, and the values together make up a feature vector 224, as shown within square brackets in the figure. Likewise, each image 225 from a melanoma training subset 227 may be associated with a value of the feature, resulting in a feature vector of values 229, as shown within square brackets. One or more probability distributions may be constructed from these values. The graph 305 shows two probability distributions (or histograms) 305a and 305b. The probability distribution 305a is constructed by forming a distribution line that connects points and that represent only values of a feature for cases belonging to the non-melanoma class. The probability histogram 305b is constructed based on values of the feature for cases that belong to the melanoma class. For some features, the histograms 305a and 305b will be non-overlapping (in some cases, substantially non-overlapping), which may suggest that values of that feature conveys information about the class (e.g., melanoma or non-melanoma) to which cases of the associated data belong. Such a feature may be useful in classification.

Returning to FIG. 1, in some implementations, at steps 115 and 120, rather than determining values of a feature associated with received training data, the first and second subsets of feature values are received. For example, rather than receiving images, one or more values of a feature of each image may be received.

Using a value of a feature associated with cases in data subsets, a score can be determined that indicates a degree to which a value of the feature can be used to predict accurately a classification of other cases (125). For example, each of a number of images of lesions may be associated with an asymmetry value. Using these values, a score can be determined that indicates a degree to which a value of a lesion's asymmetry can be used to predict accurately whether an image of a lesion indicates that the lesion is cancerous. The score may also depend on a classification of each case in the training data sets. For example, the score may depend on comparing feature values of cases with a first classification to feature values of cases with a second classification.

The score may depend on a first component that is based on the values or the distributions of the values and a second component that is also based on the values or the distributions of the values. In some cases, the two components are based in very different ways on the values or the distributions of the values (see, for example, FIG. 4, element 415). The first component may comprise a mutual-information component relating to probability distributions of values of a feature (405). In some implementations, the first component expresses the reduction in uncertainty of a value of a feature when the classification is known, relative to the value when the classification is unknown. (In some instances, "known" indicates, for example, that a case associated with a value of a feature has been classified. It does not necessarily mean that the classification was perfect.)

This change in uncertainty may be analyzed by comparing histograms (we sometimes use the terms histogram and distribution interchangeably) of the first and second subsets of feature values (which we sometimes call "conditional histograms" because they depend on which subset contains the cases being analyzed) to a combined histogram of feature values, which relates to the probability of a feature value occurring across all classes. The combined histogram may be a weighted or normalized addition of the conditional histograms (FIG. 5).

Many characteristics of distributions of values of a feature may be used to determine an uncertainty measure. For example, an uncertainty measure of a value of a feature may relate to a standard-deviation of values of the feature in the distribution, a range of the values of the feature in the distribution, an integral over a region of a histogram of the values of the feature, a maximum probability in a histogram of values of the feature, or an overlap in histograms of values of the features.

Entropy may also be used as a measure of uncertainty of a value. A total entropy H(x), which indicates the entropy of a value x of a feature, relates to the uncertainty associated with the value x when the classification is unknown. A conditional entropy H(x|y), which indicates the entropy of the value x of the feature given the classification y, relates to the uncertainty of the value x of the feature remaining if the classification is known. (See Shannon, C. E. and Weaver, W. (1949). *The mathematical theory of communication*. University of Illinois Press, Urbana, Ill., republished in 1990 by Dover Publications, Inc, and in 1998 by the University of Illinois.) These terms are mathematically defined as:

$$H(x) = -\sum_{x} p(x)\log p(x) \qquad \text{Eq. 1}$$

$$H(x|y) = -\sum_{y} q(y)\sum_{x} r(x|y)\log(r(x|y)) \qquad \text{Eq. 2}$$

where p (x) indicates the overall probability that a value of a feature is equal to x, q(y) indicates the overall probability that a classification is equal to y, and r(x|y) indicates the probability of x given the value of y. In some instances, the base of the logarithmic functions is 2, resulting in entropy and information values with units of "bits". In some instances, the base of the logarithmic functions is 10 or e.

In some implementations, a mutual-information component of the score may relate to the difference between an uncertainty when a classification is known and the uncertainty when the classification is unknown. For example, a mutual-information score component may be high when the standard deviation of values of the first and second subsets of feature values is substantially lower than the standard deviation of values of a combined set of feature values. As another example, a mutual-information score component may be high when the conditional histograms are substantially non-overlapping, as shown in FIG. 5. As another example, a mutual-information score component may be high when the total entropy of a value x of a feature is substantially higher than the conditional entropy H(x|y). A mutual information component, I(X; Y), may be defined as:

$$I(X;Y) = H(x) - H(x|y) = \sum_{y}\sum_{x} s(x,y)\log\left(\frac{s(x,y)}{p(x)q(y)}\right) \qquad \text{Eq. 3}$$

where s(x,y) indicates the joint probability of x and y (i.e., the probability both that a value of a feature is equal to x and that a classification is equal to y).

FIG. 5 shows an example in which a first histogram 502 of a first subset 504 of feature values 506 is substantially non-overlapping 508 with a second histogram 510 of a second subset 512 of feature values 514. Thus, the uncertainty 516 associated with predicting a value of a feature may be lower when the class is known as compared to when it is unknown 518. A comparison 520 of the two uncertainties yields a mutual-information score component 521 that is used in generating a combined score determination 523. This mutual-information score component 521 is higher when the difference produced by the comparison 520 is greater.

The feature-associated score may also depend on a second component, which could be any of a wide range of components that are similar to or different from the first component. For example, the second component may relate to differences between values of a feature (e.g., relating to a difference between one or more values of the first subset of feature values and one or more values of the second subset of feature values). The difference may comprise a distance between values of a feature.

The difference or distance may be based on subtracting two numbers (e.g., values of features in the first and second subsets). The difference may comprise a rounded or binned value or a difference between rounded or binned values. In some instances, a difference relates to a binary difference or a qualitative difference between values. A difference may be defined to be "1" when two values being compared are different (or when the difference between the value is above a threshold) and "0" otherwise. The difference may be defined based on pre-defined "if" statements. In some implementations, the second component depends on a difference taken to nth power or on the absolute value of a difference. An "nth-order difference" (in the numerical analysis sense) might also be considered.

In some implementations, for one or more values 506 of the first subset 504, differences 532 are calculated with respect to values 514 of the second subset 512. In some implementations, for each value of the first subset, a difference is calculated with respect to each value of the second subset (FIG. 5).

In some implementations, a subgroup of the values of the first subset is matched to a subgroup of the values of the second subset, and differences are calculated only between the matched values. (In some instances, the subgroup of values of the first subset includes all of the values of the first subset or the subgroup of values of the second subset includes all of the values of the second subset.) Factors that influence which value of the second subset should be matched to a value of a first subset may include: which second-set value is further from the first-set value, which second-set value is closest to the first-set value, which second-set value corresponds in sequential order to the first-subset value or which second-set value corresponds to a data-collection characteristic associated with the first-subset value. In some instances, each value of the first subset may be matched to no more than one value of the second subset, or each value of the second subset may be matched to no more than one value of the first subset. In some instances, each value of the first subset may be matched to any number of values of the second subset, or each value of the second subset may be matched to any number of values of the first subset.

The second component of the score may relate to unmatched values in the first or second subsets. For example, for each value in the first subset, a difference may be calculated between the first-subset value and the nearest second-subset value. However, if the difference is greater than a threshold amount, the difference may be defined to be a pre-determined amount.

The second component may comprise a distance-metric component (FIG. 4, element 410). The distance-metric component may comprise, for example, a Euclidean distance or a Minkowski distance. In some implementations, the second component comprises a Minkowski-distance metric, $L_k$, defined as:

$$L_k(x_1, x_2) = \left(\sum_{i}\sum_{j}|x_{1,i} - x_{2,j}|^k\right)^{1/k} \qquad \text{Eq. 4}$$

where $x_{1,i}$ represents a value of a feature of the ith case in the first subset of feature values and where $x_{2,j}$ represents a value of a feature of the jth case in the second subset of feature values. In some implementations, Eq. 4 includes the assessment of all pair-wise combinations of cases from the first subset of feature values with cases from the second subset of feature values. In some implementations, only a subset of such combinations is analyzed.

The metric's sensitivity to outliers may be influenced by the choice of the parameter k. If k is less than 1, the metric may be less sensitive to outliers than if k is greater than 1. k may comprise a number less than 1, a number greater than 1, 1, an integer, and/or a real number.

The distance-metric component (or another difference component) may be normalized. For example, the distance or difference may be normalized based on the total number of pair-wise differences contributing to the difference component. As some examples, a normalized Minkowski-distance metric can be defined as:

$$L_k^{norm}(x_1, x_2) = \left( \frac{\sum_i \sum_j |x_{1,i} - x_{2,j}|^k}{n_{x1} n_{x2}} \right)^{1/k} \quad \text{Eq. 5}$$

where $n_{x1}$ indicates the total number of cases in the first subset of feature values analyzed in the calculation, and $n_{x2}$ indicates the total number of cases in the second subset of feature values analyzed in the calculation.

A variety of normalization methods can be used. In some implementations, the normalization is performed by dividing the distance by the standard deviation of class one, class two, or both classes. In some implementations, the normalization is performed by dividing the distance by the variance of class one, class two, or both classes. In some implementations, the normalization is performed by dividing the distance by the mean absolute deviation of class one, class two, or both classes.

As described above, the second component may depend on a difference between a value of the first subset of feature values and a value of the second subset of feature values. However, the second component may also depend on a difference between a value of the first subset of feature values and a value of the same subset of feature values. One or more intra-set difference components may be used, for example, to normalize inter-set difference components. An intra-set difference component may include a distance metric (e.g., a normalized Minkowski-distance metric) for assessing differences within a subset of feature values. One example of an intra-set difference component is:

$$L_k^{norm}(x_1, x_1) = \left( \frac{\sum_i \sum_j |x_{1,i} - x_{1,j}|_{25}^k}{n_{x1} n_{x1}} \right)^{1/k} \quad \text{Eq. 6}$$

In some implementations, an intra-set difference component may relate to differences between values of a feature in the second subset of feature values. In some implementations, an intra-set difference component may relate to differences between values of a feature in a combined set of feature values.

In some implementations, the difference component is computed based on one or more histograms of feature values. For example, values of the first subset of feature values may be assigned to feature-value bins to create a first histogram, and values of the second subset of feature values may be assigned to feature-value bins to create a second histogram. First and second probability histograms may be determined by normalizing the respective first and second probability histograms based on the total number of feature values associated with each histogram or based on the initial sum of each histogram. Each bin of the histogram may be associated with a number. The bin-associated number may be independent of values actually assigned to the bin. For example, the bin-associated number may include a lower bound, an upper bound, or a center (midway between the upper and lower bound) of the bin. The bin-associated number may be dependent on values assigned to the bin. For example, the bin-associated number may include a minimum, a maximum, average, median, or mode value of the values assigned to the bin.

The difference component may be based on differences between bin-associated numbers of the first histogram and bin-associated numbers of the second histogram. The differences may be weighted. For example, a difference between a bin-associated number associated with a first bin of the first histogram and a bin-associated number associated with a second bin of the second histogram may be weighted based on the probability that values of the feature were assigned to the first bin in the first histogram and/or the probability that values of the feature were assigned to the second bin in the second histogram.

The difference component may be defined as:

$$L_k^{norm}(x_1, x_2) = \left( \frac{\sum_i \sum_j |b_{p1}(x_{1,i}) - b_{p2}(x_{2,j})|^k p_1(x_{1,i}) p_2(x_{2,j})}{\sum_i p_1(x_{1,i}) \sum_j p_2(x_{2,j})} \right)^{1/k} \quad \text{Eq. 7}$$

where $b_{p1}(x_{1,i})$ is equal to a bin-associated number for the first histogram and $b_{p2}(x_{2,j})$ is equal to a bin-associated number for the second histogram.

As described above, a score may be determined based on the first and second components. The score may be determined in a wide variety of ways, including, for example, based on mathematical combinations. For example, the score may depend on a product, a summation, a maximum, or a minimum of the first and second components. In some implementations, the first or second component or both may be taken to a power. In some implementations, the first or second component or both may be weighted. The score, S, may be defined as:

$$S = I(x, y)^2 \frac{L_{k1}^{norm}(x_1, x_2)}{L_k^{norm}(x_1, x_1)} \quad \text{Eq. 8}$$

In some implementation, k1 is equal to 0.5 and k2 is equal to 1.

A score (e.g., the score defined by Eq. 8) may provide a variety of advantages over other types of scores used to assess classifications. For example, scores relying only on distance measures may perform poorly for multimodal, undersampled or very noisy distributions of values of a feature. For example, the distance metric may perform poorly when a first distribution generally includes lower values of the feature and a second distribution generally includes higher values of the feature, but the second distribution also includes a low outlier. In some instances, if a score was determined only using a distance measure, a high score may result even if a distribution of values of a feature associated with one class completely overlaps with a distribution of values of a feature associated with another class, or a low score may result even if distribution of values of a feature associated with one class is completely non-overlapping with a distribution of values of a feature associated with another class. This may be problematic when attempting to compare scores associated with different features, as it can be difficult to discern whether a high score indicates that a feature is useful in determining case classifications or whether a distribution property of the training set data resulted in a high score.

Moreover, scores relying only on mutual-information measures or correlations may saturate once distributions of values of a feature for each of two classes are not overlapping. This may result in multiple "perfect" scores, again making it difficult to determine which feature to prefer. This may be particularly problematic when the number of cases in the training data are limited and the values of a feature in non-training data may stray beyond the distributions deduced from values of the feature in the training data. That is, although distributions of values of the feature may be perfectly non-overlapping in the training set, such separation may be due to the sample selected for the training data. When the distributions are further separated, it may be less likely that underlying distributions of the feature are overlapping, and thus, cases in non-training data would be easier to classify. However, because a mutual-information measure can saturate (i.e., does not continue to increase) as distributions separate, it would be difficult to distinguish features associated with histograms that are well-separated from features associated with histograms that are barely separated.

A score based both on a mutual-information component and a distance-metric component may be equal to zero when distributions are completely overlapping. Additionally, the score may continue to increase (rather than to saturate) as the distribution of values of a feature for one class is farther separated from the distribution of values of the feature for another class. Finally, by appropriately choosing k (e.g., in Eq. 5), the measure may be less sensitive to outliers. Thus, using a combination of components has advantages over using only one or the other.

As shown in FIG. 1, multiple scores may be determined, each score being associated with a feature or combination of features. Aside from depending on different features, the scores may be similarly determined (i.e., using the same equation).

A preferred feature may be identified (135, FIG. 1) based on the scores. This can be done in a wide variety of ways and combinations of ways. For example, a feature associated with the highest score may be identified as the preferred feature. In some implementations, multiple features or combinations of them may be identified as being preferred. In some examples, a score may be associated with a combination of features. Thus, if that score is considered relatively desirable (e.g., higher than others), the associated combination of features may be identified as being preferred.

In some examples, two or more scores are each associated with a single feature. A subset of the scores may be identified as desirable and the corresponding subset of features or the combination of them may be identified as preferred features. In some examples, a feature (or a combination of features) may be identified as preferred if an associated score exceeds a threshold (e.g., a pre-determined threshold). In some examples, a set of features (or combination of features) may be rank-ordered based on their associated scores. A feature (or combination of features) may be identified as preferred if it has met a ranking criterion. For example, a feature may be preferred if it is associated with one of the three highest scores.

In some cases, there may be a determination that certain features or combinations of them are not preferred relative to one another but are equally suitable.

In some implementations, a preferred type or category of feature is identified as preferred. For example, if a lesion is to be classified as being melanoma or non-melanoma, one feature may be geometric asymmetry of the lesions. However, there may be multiple ways and combinations of ways to quantify or characterize asymmetry. A score may be calculated for each type of quantification or characterization and a specific type of quantification or characterization may be identified as a preferred quantification based on the scores. A comparison of types of features may be performed separately or simultaneously to a comparison analyzing values of different features.

In some implementations, weights of features (or feature-value types) may be determined. These weights may depend on the associated scores. For example, a feature type associated with high scores may be heavily weighted.

The preferred feature (or preferred feature-value type) or one or more scores may be provided (FIG. 1, element 140). For example, the preferred feature (or preferred feature-value type) or one or more scores may be displayed on a screen, sent to a printer, or electronically transmitted to a user (e.g., by email). In some implementations, a list of features (or feature-value types) evaluated may be output along with associated scores.

The output may or may not identify a preferred feature. For example, the user may be able to recognize a preferred feature based on the scores. In some implementations, only the preferred feature (or feature-value type) is output.

The preferred feature (or preferred feature-value type) may be used to construct a classifier (FIG. 1, element 145). The classifier may receive input data comprising cases to be classified. (FIG. 6, element 605). The input data's cases may be of a similar or of the same type or types as the training data set used to determine a preferred feature or set of features or combination of features. For example, both the input data and combined training data set may consist of images of lesions. In some instances, the input data are received substantially at the same time as the training data.

For one or more cases of the input data, a value of a feature associated with each of the cases may be determined (FIG. 6, element 610). The feature may have been identified as a preferred feature. In implementations in which a preferred feature-value type was identified, a value of the preferred type may be determined for one or more cases of the input data. In some implementations, the value of a feature is received as an input, and so the value need not be determined. In implementations in which multiple features were identified as preferred, values of each feature may be determined for each case.

In some implementations, values of multiple features are input to the classifier. Thus, determining the value of the feature (610) may comprise selecting a value associated with a preferred feature.

In some implementations, values for multiple features are determined. For example, in some instances, a value is determined for each feature to be associated with a score.

The input data may be classified based on the value of the preferred feature (615). A wide variety of classifiers or combinations of classifiers may be used to classify the input data. For example, the classifier may use a nearest-neighbor technique, a maximum-likelihood technique, or a mutual-information-maximization technique. In some implementations, the preferred feature is associated with an initial condition for the classifier. The classifier may then evolve or "learn" to use other features to perform the classification. The classifier may comprise a learning-based classifier.

In some implementations, the input data is classified based on multiple features. For example, the input data may be classified based on all features that are associated with a score. The classification may weight the importance of the features based on weights associated with respective features. That is, features that were associated with desirable (e.g., higher) scores may be more heavily weighted in the classification.

The number of features used in the classification may depend on a number of cases in one or more data sets. For example, in some implementations, the number of features is constrained to be less than the total number of cases from the training data sets. In some implementations, the number of features is constrained to be less than half of the total number of cases from the training data sets. In some implementations, the number of features is constrained to be less than the minimum number of cases from the training data sets having any one classification.

In some implementations, the classifier uses part or all of the training data set. For example, cases from the training data set may be used to form templates associated with all possible classes. A nearest-neighbor algorithm could then determine a classification by comparing a value of a preferred feature of an input (testing) data case to that in the templates. As another example, a nearest-neighbor algorithm could determine a classification by comparing a value of a preferred feature of an input (testing) data case to all training-data cases. The classification assigned to the input testing data case may then be the same as the classification of the training-data case which was identified to be the nearest neighbor in this analysis. In other implementations, the classifier does not use the training data set.

Once one or more preferred features have been identified (and, if relevant, weights to one or more features have been assigned), a performance-prediction estimate may be determined for the classifier. For example, using the one or more preferred features (and weights assigned to one or more features), a classifier may classify all or some of the cases in the training data set. The performance-prediction estimate may relate to the proportion of correctly classified cases. In some instances, various fractions of the cases in the training data set are analyzed, and the performance-prediction estimate relates to extrapolating an accuracy percentage to a data set of infinite size. In some implementations, an initial training data set is subdivided, a first fraction of the training data set is used to determine one or more preferred features (and weights assigned to one or more features), and a second fraction of the training data set is used to determine a performance-prediction estimate.

Additionally, if the preferred features (or weights assigned to one or more features) are repeatedly identified using different subsets of cases from an initial training data set, a "reliability" of the identification of the preferred features, associated scores, or weights assigned to one or more features, may be determined. In some implementations, a feature may be identified to be preferred only if it is identified as "preferred" in a threshold percentage of these repeated processes. In some implementations, weights associated with features are determined by averaging weights determined in successive process runs.

In some implementations, a score associated with a preferred feature may be indicative of or a prediction of a performance of the classifier. For example, if the preferred feature were associated with a low score, it may be predicted that the classifier would not be able to accurately classify a substantial proportion of cases.

The approaches described above may be applied to classification in a wide variety of medical fields and other fields. For example, by determining one or more scores in the way described here, features may be identified that are more highly indicative of a disease, prognosis, or diagnosis. In some implementations, a case includes an image (e.g., of a skin lesion, a skin condition, a swollen body part, a retina, vasculature, or an MRI image), a number (e.g., related to a blood test), a radiograph, a magnetic signal, or an electrical signal (e.g., related to an EKG, ECG or EEG). Cases in training data sets may be classified based on, for example, human classification (e.g., a doctor's diagnosis), an automated classification, or a post-hoc diagnosis determination, or some combination of those or other techniques.

In some implementations, classifications can relate to evolutionary algorithms, such as a genetic algorithm, genetic programming, or linear genetic programming, or a combination of them. In some implementations, a case includes a string of numbers (e.g., representing chromosome information), a genetic sequence, or a gene-expression profile or a combination of them. Training data sets, for example, may include cases comprising non-optimal solutions (class 1) and optimal solutions (class 2). One or more preferred features may be identified, and these features may be used to evaluate the fitness of a test case. Test cases with high fitness may then "mutate" or "reproduce" in a genetic algorithm. Thus, pairings, mutations, or initial cases that may lead to an optimal solution may be identified.

In some implementations, a case involves multiple nodes or operators, each executing a computational function. For example, a first node in a case may represent a subtraction, a second node may represent a log function, etc. Features may relate to node computations. For example, one feature may be whether or not any node in the case involves a power function, another feature may relate an exponent in a power-law relation, another feature may relate to a whether a subtraction node follows a logarithmic node, etc. For each case, the classification may depend on whether the output of the associated node computations matches a desired (e.g., a user-defined) output or objective. In some instances, different cases may also relate to different inputs or initial states. Scores may then be compared across features, as described above. A fitness score may be calculated for each case by comparing the nodes in the case to the criteria associated with the preferred feature. New computer programs may then be created based on reproducing and mutating high-fitness cases. For example, a user may input a number of cases, each including parameters related to a driving condition. Each case may be associated with a desired car-related output (e.g., a desired speed). A new computer program may be created that uses input parameters to determine the car's speed.

In some implementations, a case involves a series of instructions (e.g., for a computer program). Features may be related to specific instructions, blocks of instructions, or instruction types. The instructions may, for example, include mathematical operations. For each case, the classification may depend on whether the output of the associated node computations matches a desired (e.g., a user-defined) output or objective. In some instances, different cases may also relate to different inputs or initial states. Scores may then be compared across features, as described above. A fitness score may be calculated for each case by comparing the nodes in the case to the criteria associated with the preferred feature. New computer programs may then be created based on reproducing and mutating high-fitness cases. For example, a user may input a number of cases, each including parameters related to a potential oil-drilling site. Each case may be associated with an outcome as to whether oil was found at the site or the pressure of oil found. A new computer program may be created that uses input parameters to predict the presence of oil or oil pressure.

In some implementations, cases are classified based on two possible classes. In some implementations, there may be more than two classes, for example, classes that relate to stages of cancer or susceptibility to a different treatment options. The equations may be modified or applied to such implementations in which there are more than two classes. For example, the Minkowski-distance metric, $L_k$, defined in Eq. 4 may be modified as follows when three classes exist:

$$L_k(x_1, x_2, x_3) = \qquad \text{Eq. 9}$$

$$\left( \sum_i \sum_j |x_{1,i} - x_{2,j}|^k + \sum_i \sum_m |x_{1,i} - x_{3,m}|^k + \sum_m \sum_j |x_{3,m} - x_{2,j}|^k \right)^{1/k}$$

In some implementations, the Minkowski-distance metric, $L_k$, may be divided by the number of inter-set comparisons, which, in this example would be 3.

The techniques described can be implemented in digital electronic circuitry, or in computer hardware, firmware, software, or in combinations of them. The techniques can be implemented as a computer-program product, i.e., a computer program tangibly embodied in an information carrier, e.g., in a machine-readable storage device or in a propagated signal, for execution by, or to control the operation of, a data-processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps described above can be performed by one or more programmable processors executing a computer program to perform functions of the invention by operating on input data and generating output. Method steps can also be performed by, and apparatus of the invention can be implemented as, special-purpose logic circuitry, e.g., an FPGA (field-programmable gate array) or an ASIC (application-specific integrated circuit). Modules can refer to portions of the computer program or the processor/special circuitry that implements that functionality.

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

To provide for interaction with a user, the techniques that we describe can be implemented on a computer having a display device, e.g., a CRT (cathode-ray tube) or LCD (liquid-crystal display) monitor, for displaying information to the user and a keyboard and a pointing device, e.g., a mouse or a trackball, by which the user can provide input to the computer (e.g., interact with a user interface element, for example, by clicking a button on such a pointing device). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input (e.g., a "touch screen").

The techniques can be implemented in a distributed computing system that includes a back-end component, e.g., as a data server, or a middleware component, e.g., an application server, or a front-end component, e.g., a client computer having a graphical user interface or a Web browser through which a user can interact with an implementation of the invention, or any combination of such back-end, middleware, or front-end components. The components of the system can be interconnected by any form or medium of digital data communication, e.g., a communication network. Examples of communication networks include a local-area network ("LAN") and a wide-area network ("WAN"), e.g., the Internet, and include both wired and wireless networks.

FIG. 7 shows an example computer system 700 that may be used to perform the techniques described above. The system 700 may include a system unit may, which may include a central processing unit 710 and a memory 715 (e.g., a read-only memory or a random-access memory or both). The computer system 700 may include one or more input components 720, such as a CD drive 720a, a CD/DVD drive, a DVD drive, a floppy-disk drive 720b, or a USB port 720c. The computer system 700 may include one or more user-input devices 725, such as a keyboard 725a, a mouse 725b, or a touch screen 730a. The computer system 700 may include a display, such as a monitor 730. The computer system may be connected to one or more external devices 735, such as a camera 735a or a scanner 735b. The computer system 700 may also include a modem, which may be configured to connect the system 700 to a communication network. The computer system 700 may also include a printer.

In some implementations, the computer system 700 may receive a training data set or a testing data set from one or more input devices 735. For example, the camera 735a may be used to capture images of patients' skin lesions or a microphone may be used to record sounds (e.g., that may include a human speaking) The data may then be transferred from the camera 735a to the computer system (e.g., via a USB cable). In other implementations, images are scanned into the computer system using the scanner 735b. In other implementations, data are stored on a storage device, such as a CD, a DVD (790a), a floppy disk (790b), or a USB stick (790c). The computer system may then receive the data through one or more input components 720. In some implementations, the computer system itself determines values of a feature based on received data. In some implementations, values of features are input into the computer. For example, the values may be stored on a storage device 790 (e.g., a CD 790a, a DVD, a floppy disk 790b, a USB drive 790c, or an external hard drive 790d) and received by the computer system from one or more input components 720. As another example, a user may input the values, e.g., using one or more user-input devices 725. Outputs (e.g., an identified preferred feature, a score, or classification of testing data) may be output to the user, e.g., by a display (730). The outputs may also be printed or written to a storage device 790, such as a CD, a DVD, a floppy disk, or a USB stick. The outputs may also be transmitted over a network.

Other implementations are within the scope of the following claims and other claims to which the applicant may be entitled. The steps described above can be performed in a different order and still achieve desirable results.

In some examples of the techniques described above, a Monte-Carlo method can be used to generate values of a feature for a first class based on a pre-determined mean, variance, and distribution shape associated with the class. Similarly, using a Monte-Carlo method, values of a feature for a second class are generated based on a pre-determined mean, variance, and distribution shape associated with the class. The values of the feature are regenerated for each of 1000 "sweeps", in which the relative means of the distributions change across the sweeps. FIG. 8 shows distributions of the values of a feature for both classes for 10 of the 1000 sweeps (corresponding to sweep indexes 0, 100, 200, 300, 400, 500, 600, 700, 800 and 900). As shown, the distributions are non-overlapping for low-index and high-index sweeps (see, e.g., FIG. 8a and FIG. 8j), but the distributions are substantially overlapping for middle-index sweeps (see, e.g., FIG. 8f).

FIG. 9a shows a score, calculated using Eq. 8, as proposed here, as a function of sweep index. The score is high for low-index and high-index sweeps but is near zero for middle-index sweeps. Comparison scores are also calculated for each sweep.

For comparison, FIG. 9b shows an area under the curve of the receiver-operating characteristic (ROC). For each sweep, an ROC curve is calculated by plotting a "hit rate" to a "false alarm rate" for a range of thresholds. Each point along the curve corresponds to a different threshold, and values above the threshold are given one classification while values below the threshold are given the other. If the distributions are completely non-overlapping, a low threshold (below both distributions) will result in a hit rate of 1 and a false-alarm rate of 1. As the threshold increases through the values associated with the lower distribution, the false-alarm rate will decrease (ultimately to 0) but the hit rate will remain at 1. As the threshold further increases through the values of the higher distribution, the hit rate begins to decrease to 0. Thus, for perfectly non-overlapping distributions, the ROC curve consists of a line from (0,0) to (0,1) and a line from (0,1) to (1,1), and the area under the curve is equal to 1. For perfectly overlapping distributions, changes in the hit rate are mirrored by changes in the false-alarm rate. Thus, the curve consists of a line from (0,0) to (1,1), and the area under the curve is equal to 0.5.

FIG. 9c shows a correlation using a Pearson correlation coefficient, which relates to the covariance in the values of the features (x) with the classification (y). Mathematically, the Pearson correlation coefficient is estimated as:

$$r = \frac{\sum_j (\overline{x_j} - \overline{x})^2}{\sum_j \sum_i (x_{ij} - \overline{x_j})^2}$$ Eq. 10

(from Dhirl, C. S., Iqball, N., & Lee, S.-Y. (2007). Efficient feature selection based on information gain. *Proceedings of the 2007 International Conference on Information Acquisition*, 523-527)

When the distributions are non-overlapping, the classifications change with the values of the feature and the covariance of x and y is high. For example, if high values of a feature are associated with a classification of "1" and low values of the feature are associated with a classification of "0", then the numerator of Eq. 10 will consist of a summation of positive terms (arising either from the multiplication of two positive numbers or of two negative numbers). When the distributions are completely overlapping, the covariance is low, as terms in the numerator are equally likely be positive or negative. In this example, the correlation coefficient reaches zero for overlapping distributions.

FIG. 9d shows the mutual information between the feature and the class identification. The mutual information measure was calculated as defined in Eq. 3. As described above, when distributions of values of a feature are non-overlapping, then knowing the classification associated with each value reduces the entropy of the value, resulting in a high mutual-information measure. When distributions of values of a feature are completely overlapping, knowledge of the classifications do not decrease the entropy of the value, resulting in a mutual-information measure of zero.

FIG. 9e shows the pair-wise Euclidean distance between values of the two classes. The Euclidean distance was calculated as defined in Eq. 5, where k is equal to 2. When the distributions are completely non-overlapping, the distance from values of a feature associated to a first class with values of a feature associated with a second class is high. Unlike the separation measures in FIGS. 9b-9d, the Euclidean distance does not saturate: as the distributions further separate from each other, the distance continues to increase.

FIG. 9g shows the margin distance, which is related to the differences between values of opposite classes that are closest to one another. Mathematically, the difference is defined as:

$$m = \min(b_{x_1,j} - b_{x_2,j})$$ Eq. 11 where b is the histogram bin center.

Additionally, as with the pair-wise Euclidean distance, the margin distance does not saturate once the distributions are non-overlapping.

Figure 1:
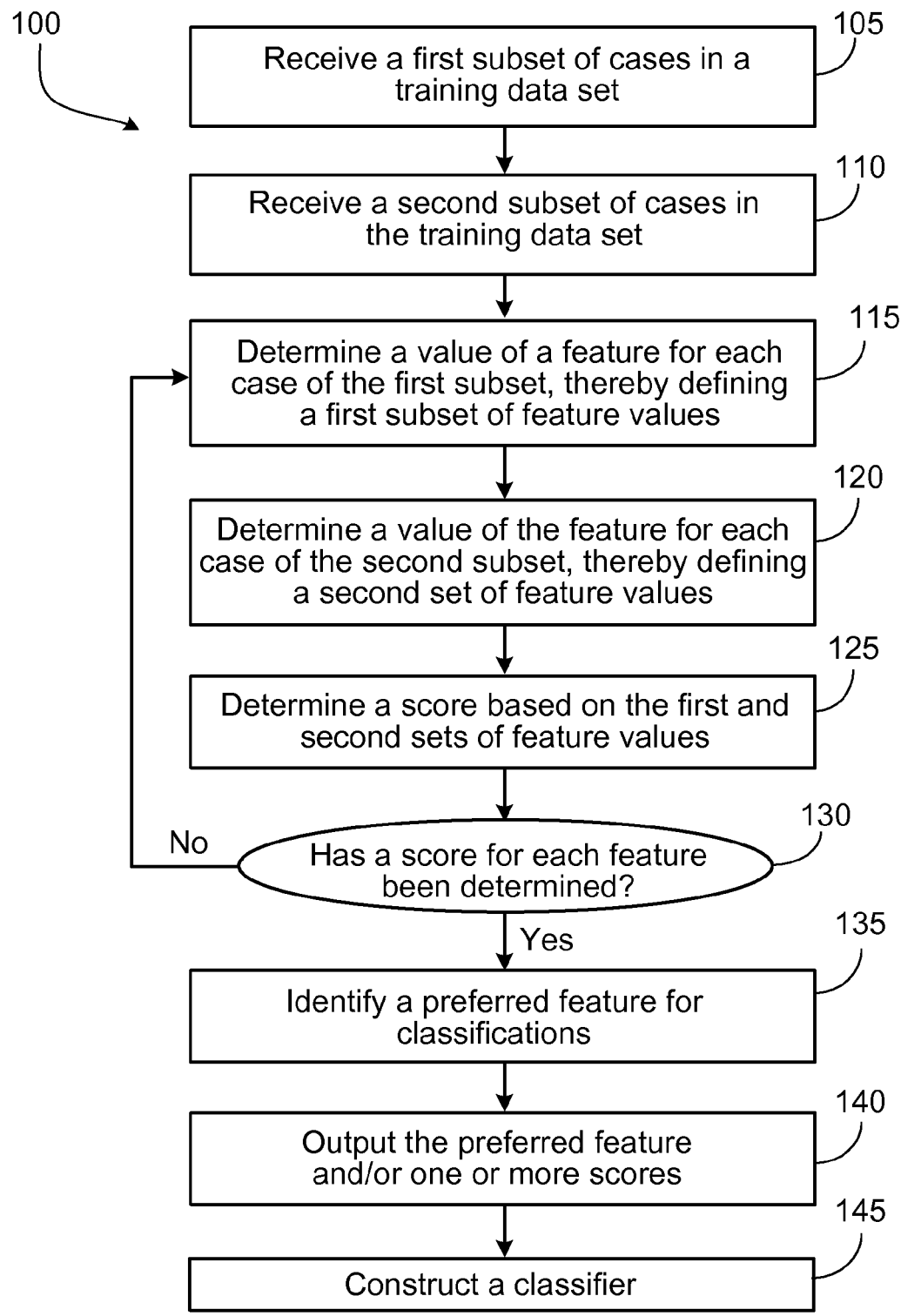
Figure 2:
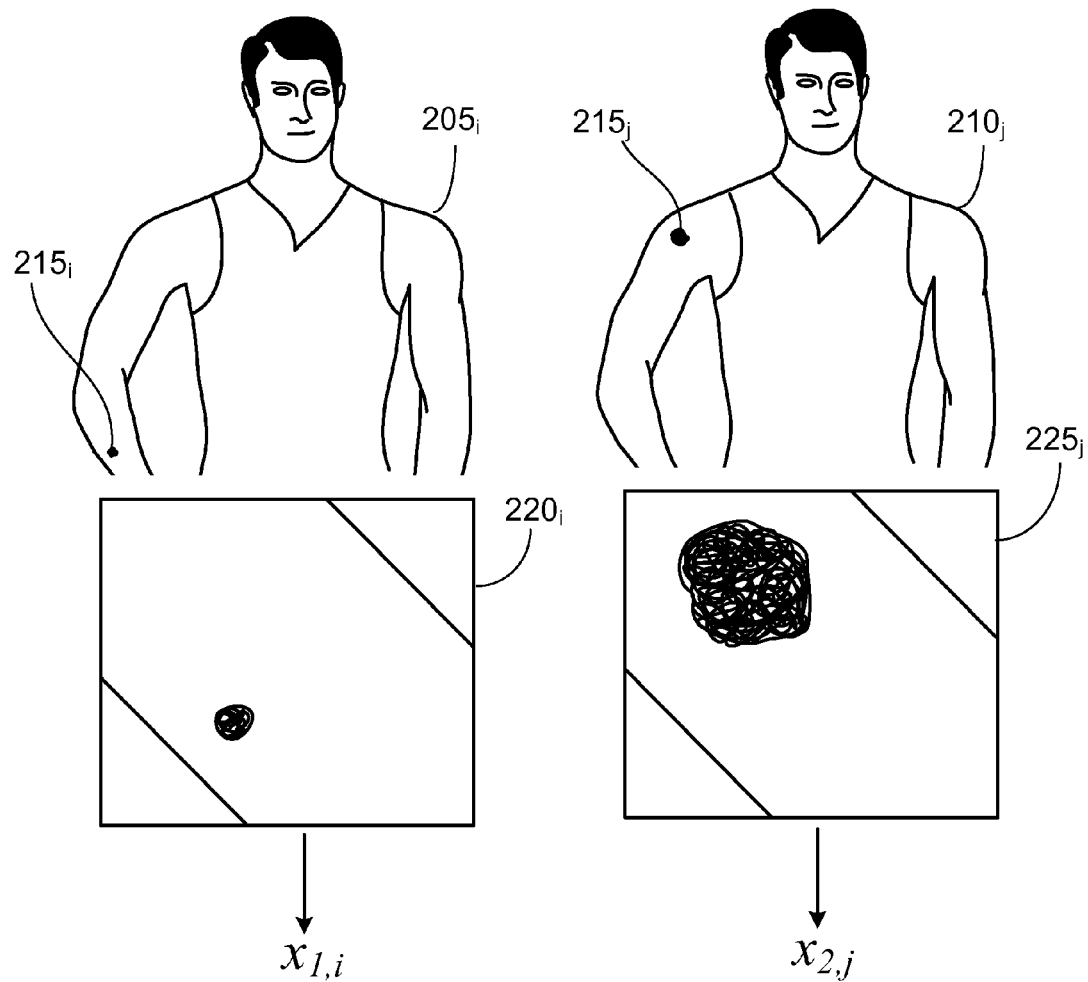
Figure 3:
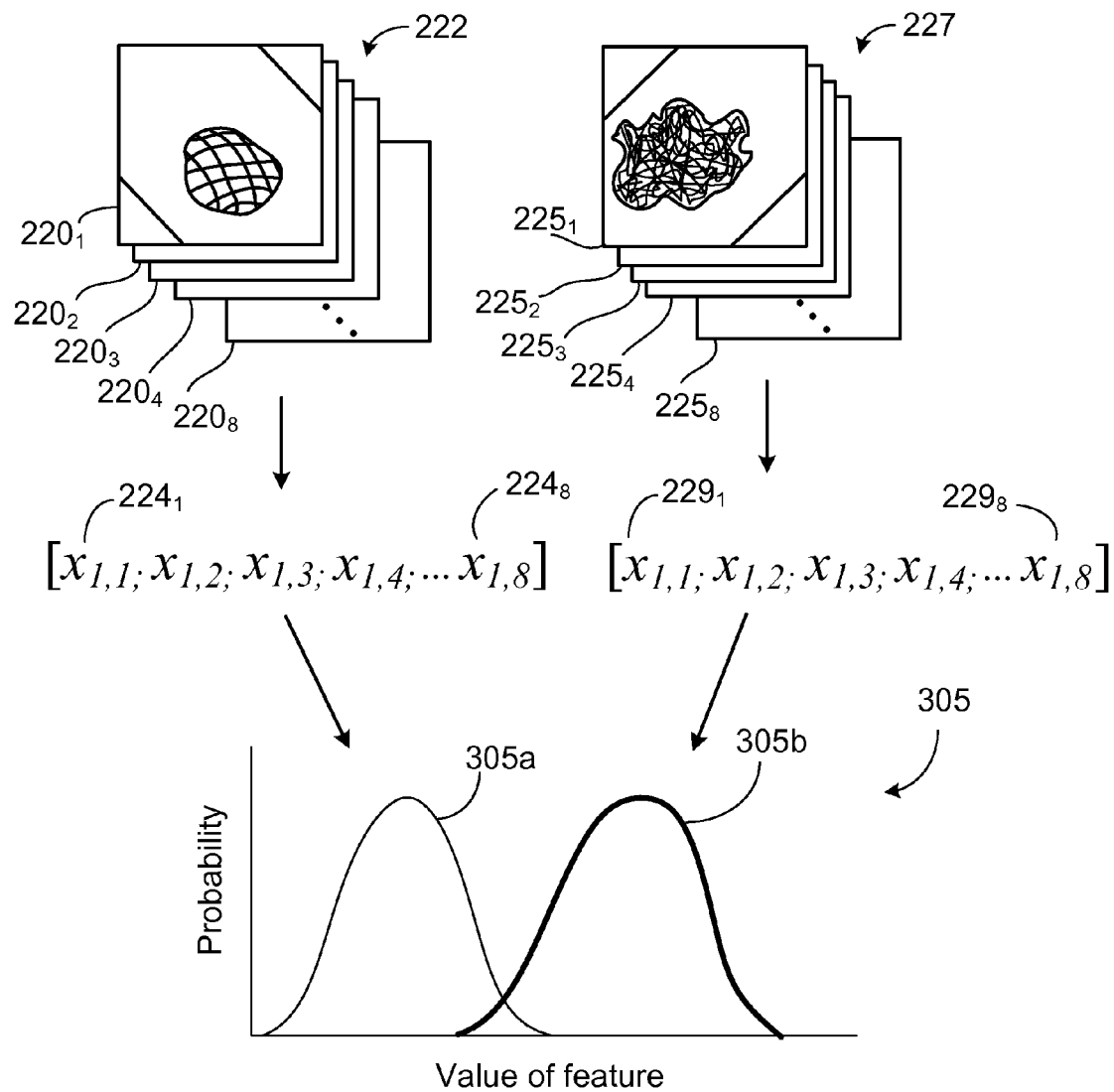
Figure 4:
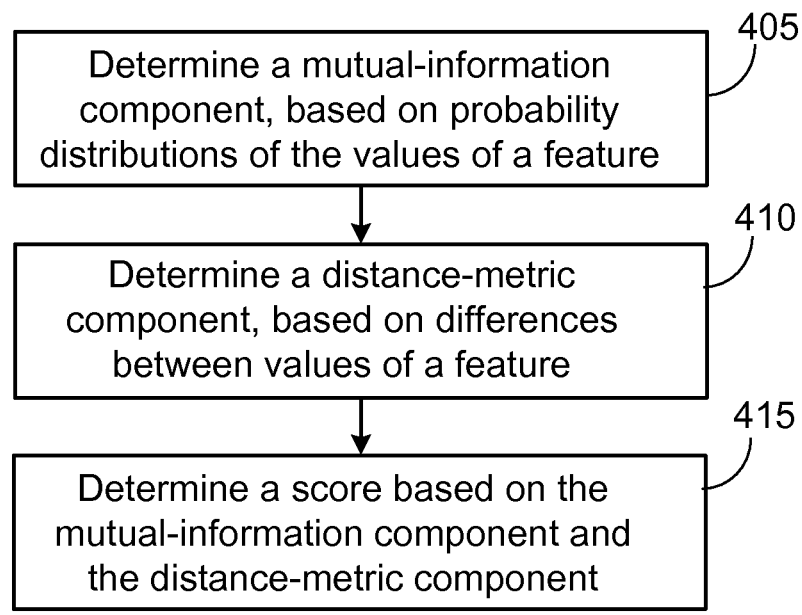
Figure 5:
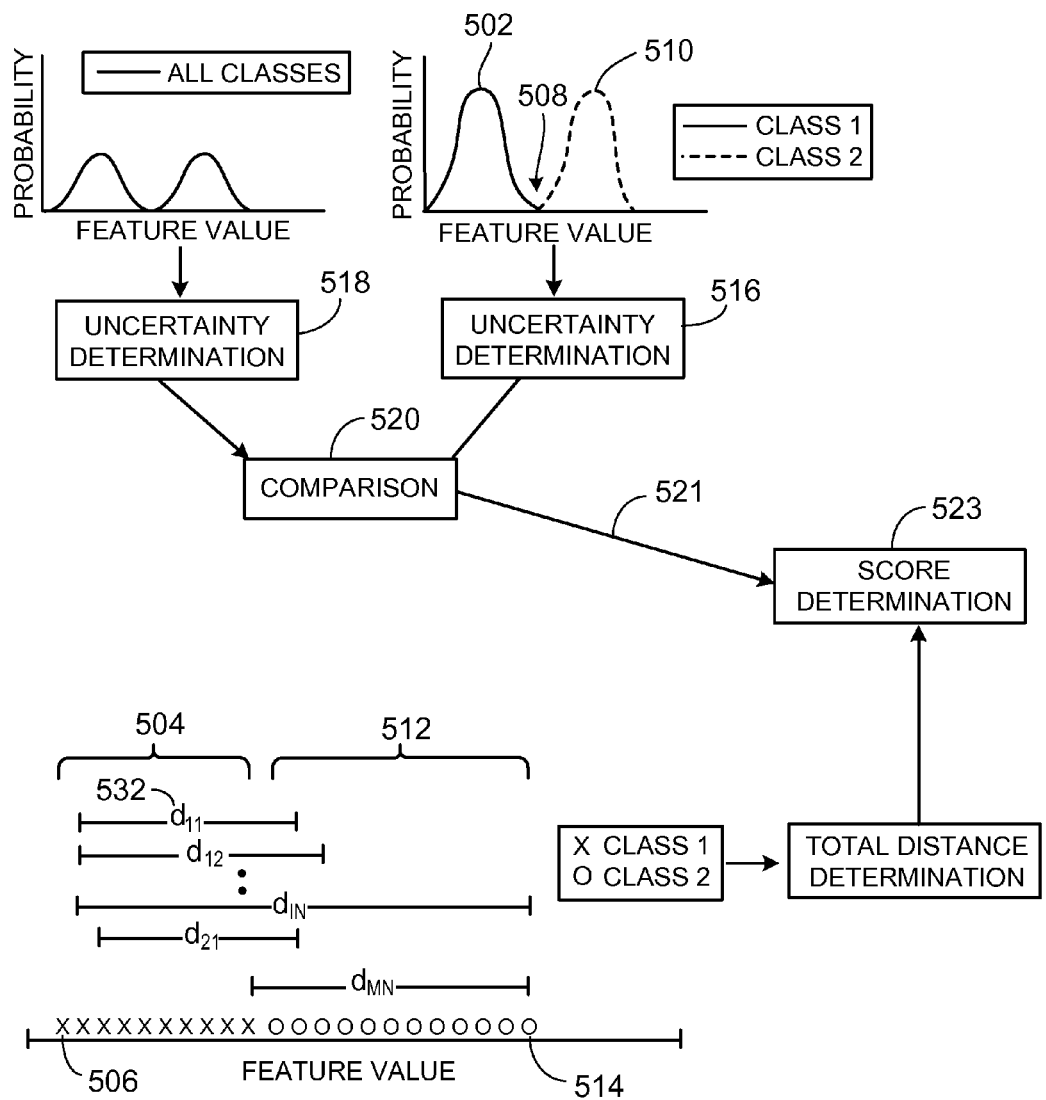
Figure 6:
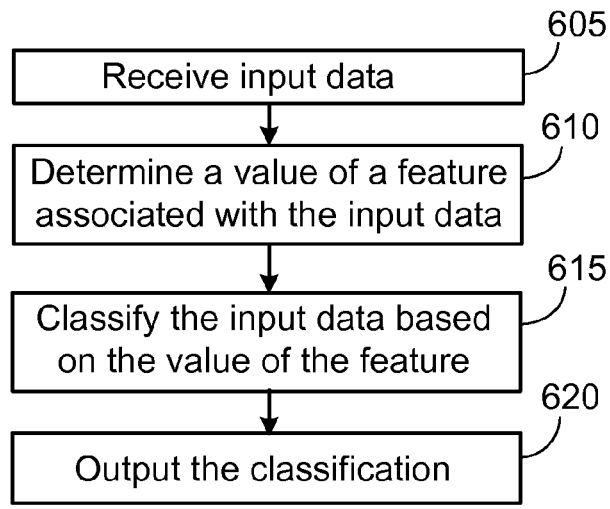
Figure 7:
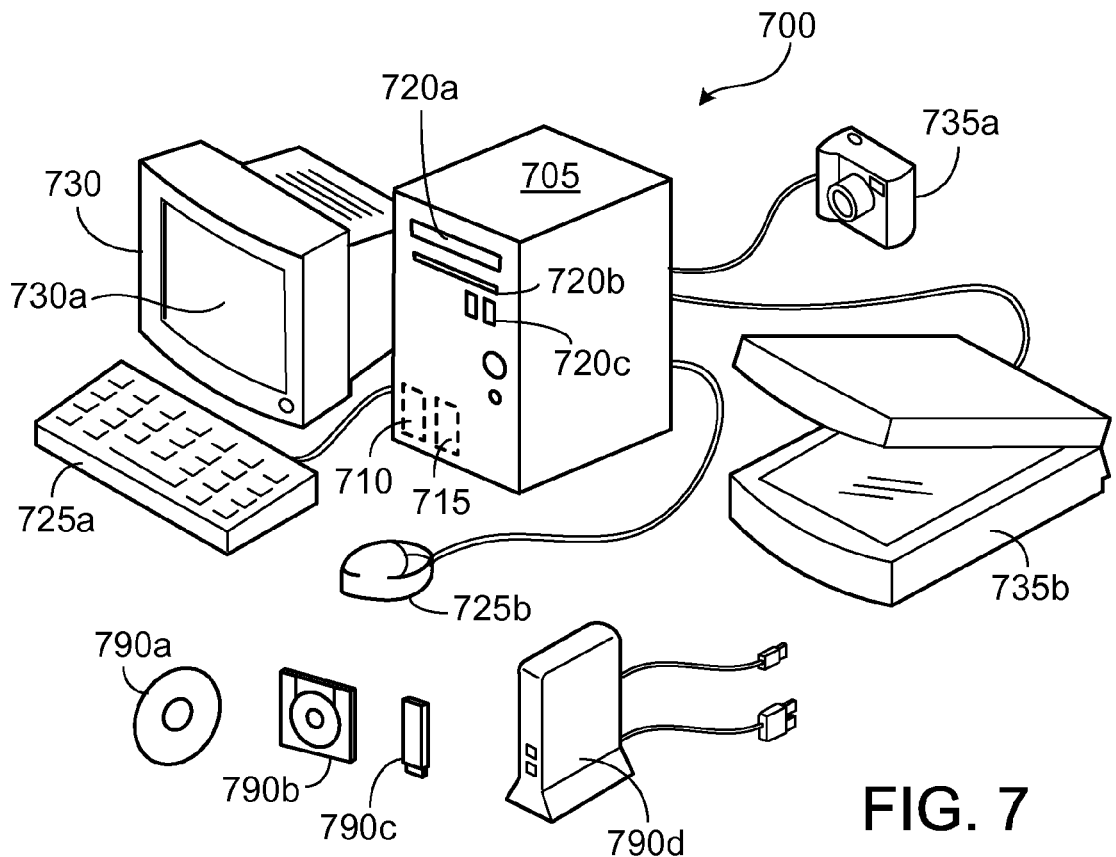
Figure 8A:
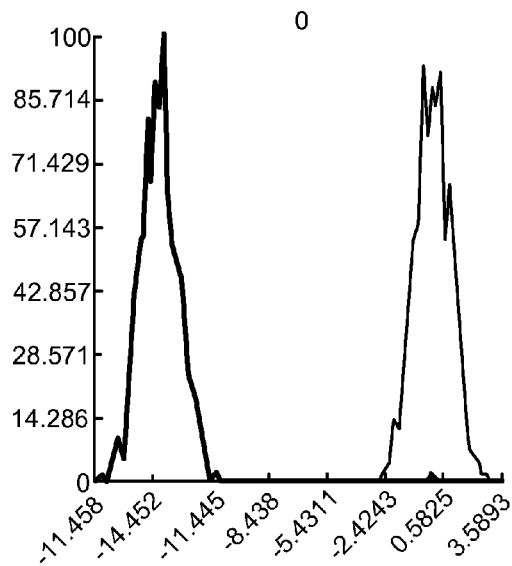
Figure 8B:
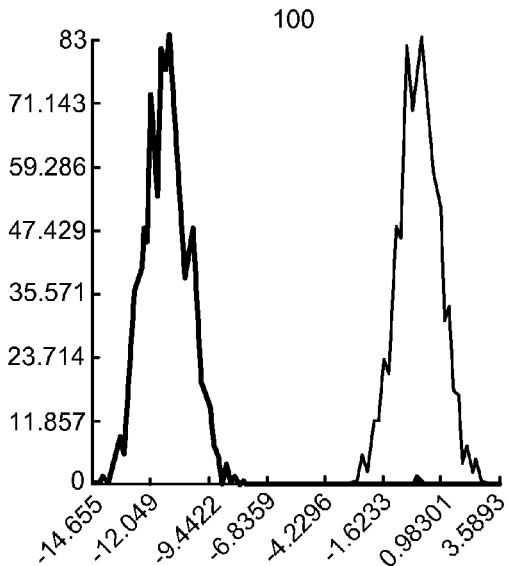
Figure 8C:
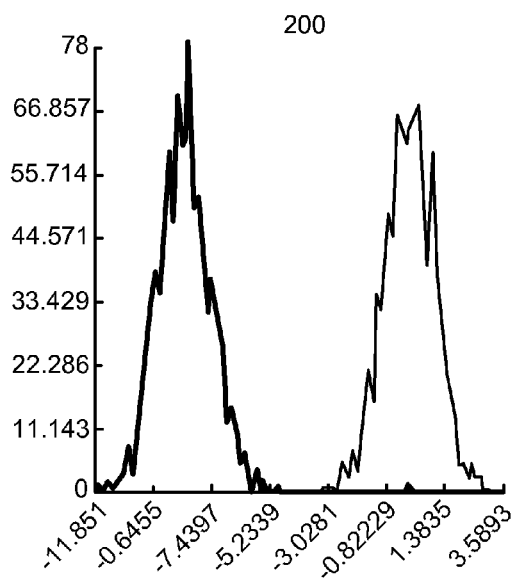
Figure 8D:
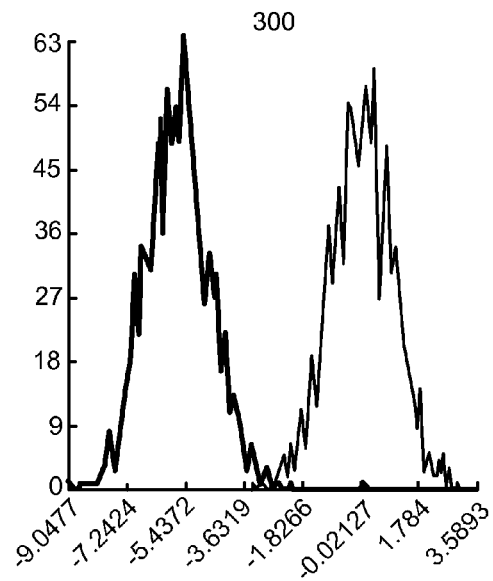
Figure 8E:
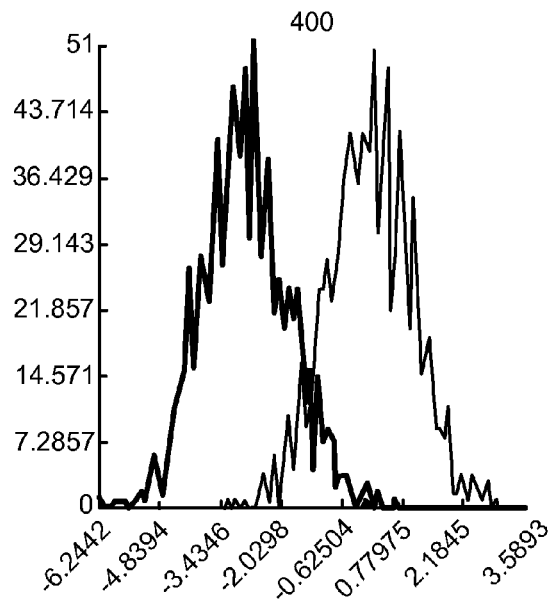
Figure 8F:
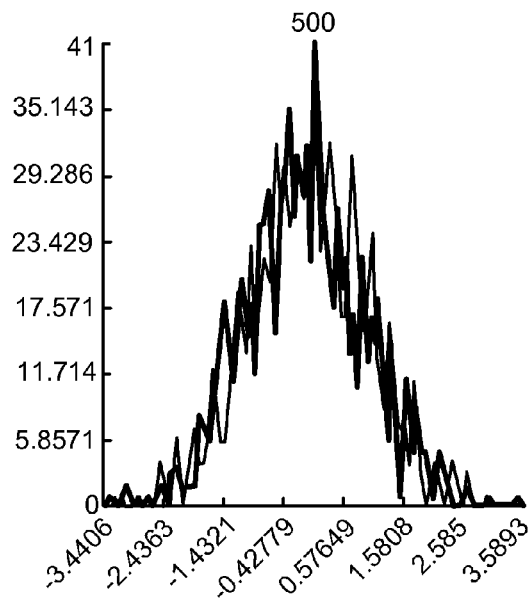
Figure 8G:
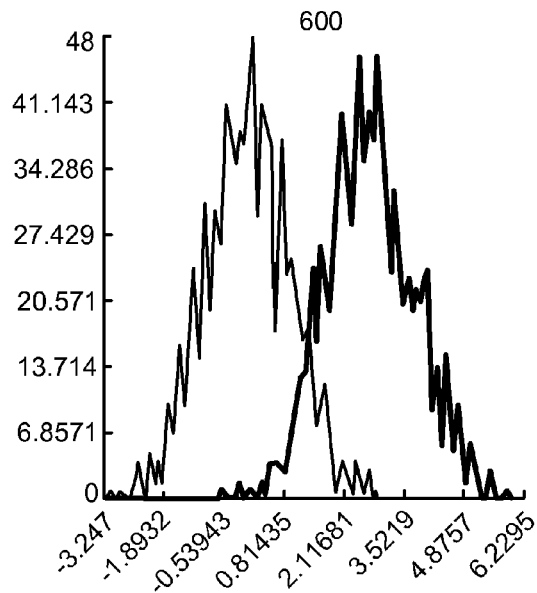
Figure 8H:
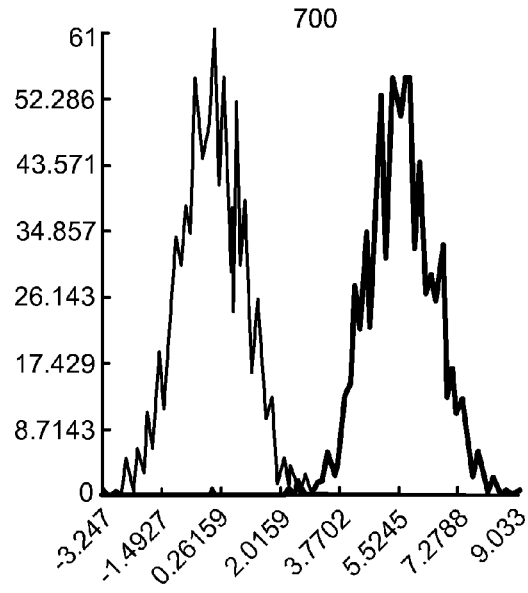
Figure 8I:
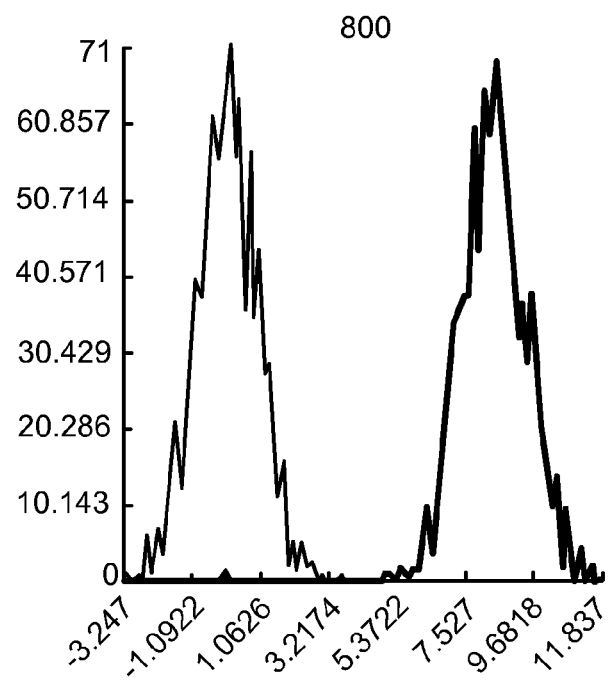
Figure 8J:
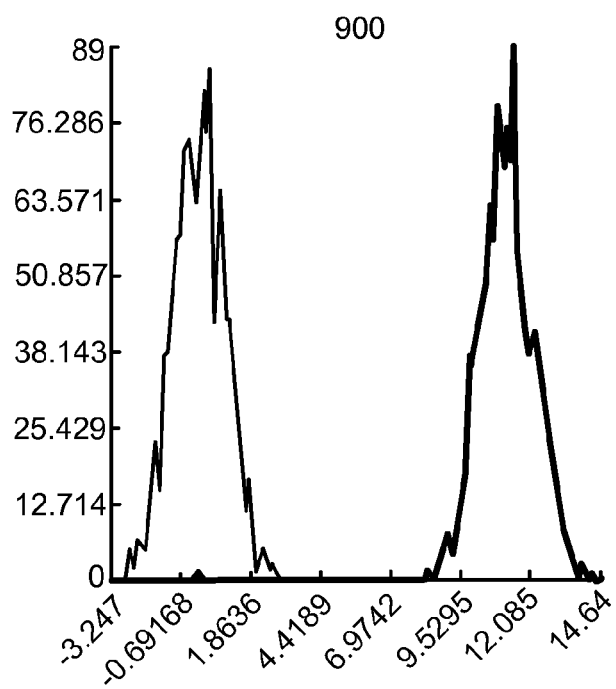
Figure 9E:
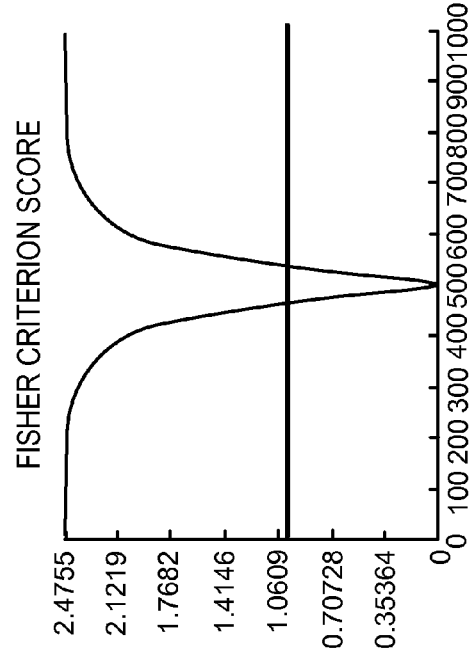
Figure 9F:
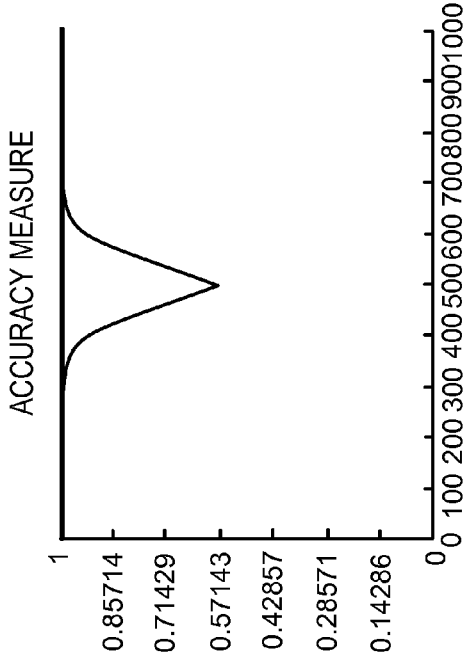
FIG. 9f shows Fisher's criterion score, which relates to a between-class variance relative to a within-class variance.
Figure 9G:
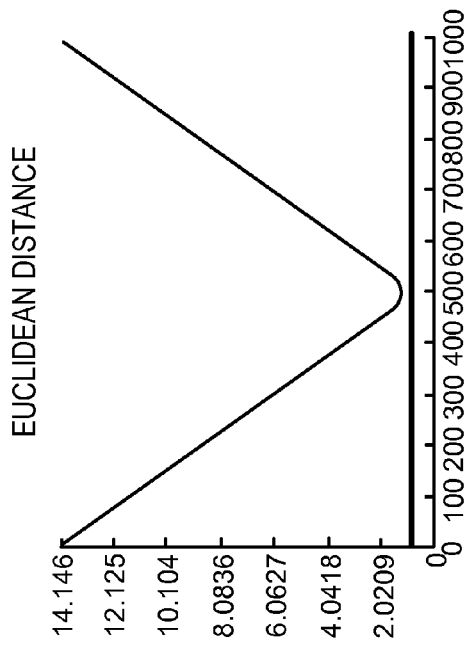
Figure 9H:
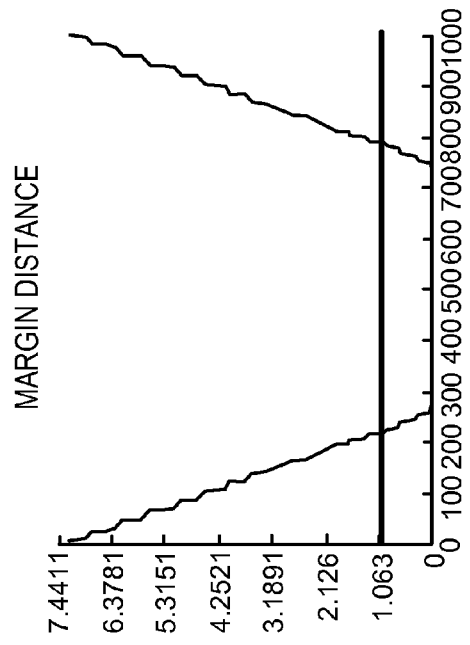
Figure 10:
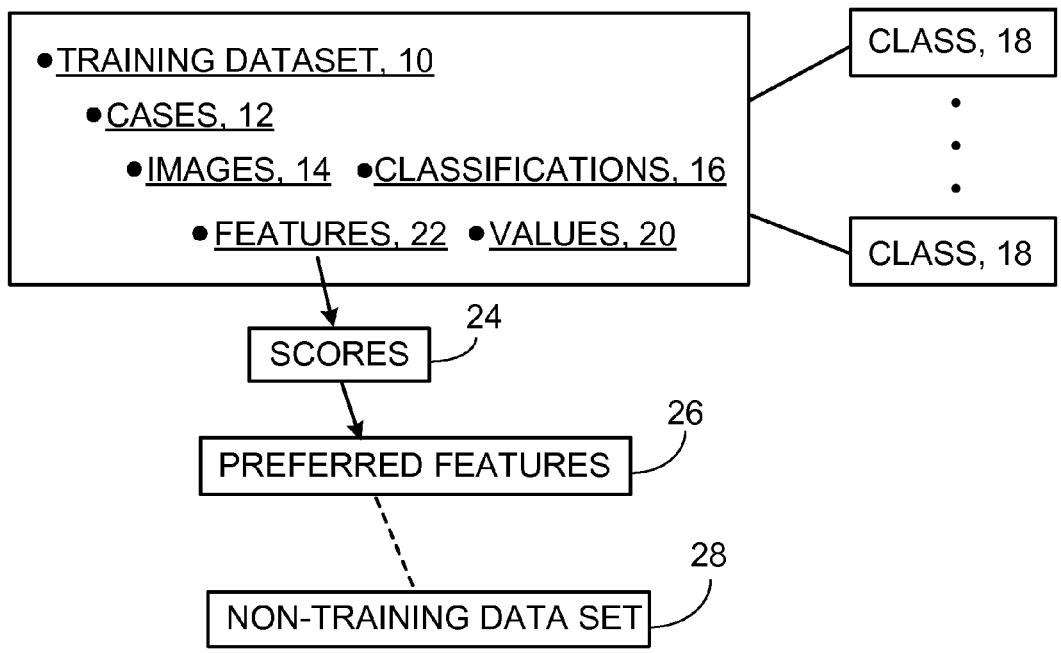

FIG. 9h shows the maximum theoretical accuracy. To calculate the maximum theoretical accuracy, each bin of the histogram is assigned to one of the two classes, the assigned class being the class with more samples in the bin. Samples (from both distributions) in that bin were then associated with the assigned class. The accuracy is equal to the percentage of all samples which were correctly associated with their true class. Thus, in this case, even when the distributions are completely overlapping, the maximum theoretical accuracy is equal to 0.5, as there is 0.5 probability of correctly predicting the class. For non-overlapping distributions, the maximum theoretical accuracy reaches 1.0.

Pearson's correlation coefficient, the area under the curve of the ROC, the mutual information, Fisher's criterion, and the margin distance are described in Guyon, I. & Elisseeff, A. (2003). An Introduction to Variable and Feature Selection. *Journal of Machine Learning Research* 3, 1157-1182. Fisher's criterion is described in Guyon & Elisseeff and is implemented as described in Dhirl, C. S., Iqball, N., & Lee, S. Y. (2007). Efficient feature selection based on information gain, *Proceedings of the 2007 International Conference on Information Acquisition*, 523-527. The pair-wise Euclidean distance is described in Dash, M. & Liu, H. (1997). Feature Selection for Classification. *Intelligent Data Analysis: An International Journal*, 1, 131-156 and in Duda, R. O. Hart, P.

E., & Stork, D. G. (2001). *Pattern Classification*. 2$^{nd}$ ed. Wiley-Interscience, 632. The Minkowski distance is described in Duda, Hart, et al., 188. All references cited in this document are incorporated here by reference in their entireties.

The score calculated from Eq. 8 is not subject to saturation, while the ROC area, correlation, mutual information, and Fisher-criterion score do show saturation at high and low sweep counts. Further, the score calculated from Eq. 8 is near zero when the distributions are overlapping, while the ROC area and Euclidean distance remain substantially above zero during the middle sweep counts. Finally, the score calculated from Eq. 8 is equal to non-zero values while only a portion of the distributions are overlapping (see, e.g., sweep counts 300 and 700), while the margin distance remains at zero even while the overlap between the distributions is relatively small.

When we use the word in a list such as A, B, or C, we typically mean to include any one of, and any combination of two or more of, the items in the list.

Other implementations are within the scope of the following claims.

What is claimed is:

1. A computer-implemented method comprising:
   determining, by a processor, a degree to which values of a feature that characterizes cases correctly predict classes to which the cases belong, the degree depending on a mathematical combination of at least two factors that include:
   (a) uncertainty about the values that the feature will have depending on knowledge about classes to which the cases belong, wherein the uncertainty comprises an entropy of the values of the feature, and
   (b) comparison of one or more first values of the feature that are associated with cases that belong to a first class with one or more second values of the feature associated with cases belonging to a second class.

2. The method of claim 1 in which the uncertainty is represented by a mutual information measure.

3. The method of claim 1 in which the comparison comprises a distance measure.

4. The method of claim 3 in which the distance measure is normalized.

5. The method of claim 1 in which the uncertainty about the values of the feature comprises an uncertainty when the classes to which the cases belong are known, and an uncertainty when the classes to which the cases belong are not known.

6. The method of claim 1, in which the degree is determined as a score.

7. The method of claim 1, in which the comparison of one or more first values of the feature with one or more second values of the feature comprises determining differences between first values and second values.

8. The method of claim 1, in which the comparison of one or more first values of the feature with one or more second values of the feature comprises a comparison of a first value of the feature with two or more second values of the feature.

9. The method of claim 1, in which the degree is determined with respect to values of more than one such feature, the degree depending on:
   (a) uncertainty about values that the more than one such feature will have depending on the classes to which cases belong, and
   (b) comparison of one or more first values of the more than one such feature that are associated with cases that belong to a first class with one or more second values of the more than one such feature associated with cases belonging to a second class.

10. The method of claim 3, in which the comparison comprises a metric distance between the one or more first values of the feature and the one or more second values of the feature.

11. The method of claim 1, in which the cases comprise medical cases.

12. The method of claim 1 in which the cases comprise communication cases.

13. The method of claim 1 in which the cases comprise computer-vision cases.

14. The method of claim 1 in which the cases comprise computer-security cases.

15. The method of claim 1 in which the cases comprise voice-recognition cases.

16. The method of claim 1 in which the cases comprise genetic cases.

17. The method of claim 10, in which the cases comprise skin lesions and the classes include melanoma and non-melanoma.

18. The method of claim 1, further comprising:
   determining a first degree to which a value of a first feature that characterizes cases correctly predicts classes to which a particular case belongs;
   determining a second degree to which a value of a second feature that characterizes cases correctly predicts classes to which a particular case belongs; and
   comparing the determined first and second degrees.

19. The method of claim 1, further including:
   selecting a feature for use in classification, based at least in part on the determination of the degree.

20. The method of claim 1, in which the cases are represented by digital images and the features relate to what is portrayed in the digital images.

21. The method of claim 20, in which the values comprise measures of features that appear in the digital images.

22. The method of claim 1 in which the uncertainty is represented by an accuracy measure.

23. The method of claim 1 in which the degree is determined based on a single calculation that uses at least the factors (a) and (b).

* * * * *